United States Patent
Liechtung (10) Patent No.: US 7,357,637 B2
(45) Date of Patent: Apr. 15, 2008

(54) DENTAL APPLIANCE

(75) Inventor: M. Marc Liechtung, Brooklyn, NY (US)

(73) Assignee: Snap On Smile LLC, New York, NY (US)

( * ) Notice: Subject to any disclaimer, the term of this patent is extended or adjusted under 35 U.S.C. 154(b) by 0 days.

(21) Appl. No.: 11/232,641

(22) Filed: Sep. 22, 2005

(65) Prior Publication Data

US 2006/0216670 A1  Sep. 28, 2006

Related U.S. Application Data (60) Provisional application No. 60/666,203, filed on Mar. 28, 2005, provisional application No. 60/665,343, filed on Mar. 25, 2005.

(51) Int. Cl.
*A61C 13/00* (2006.01)

(52) U.S. Cl. .................................................. 433/167

(58) Field of Classification Search ................ 433/167, 433/171, 215, 196, 202.1
See application file for complete search history.

(56) References Cited

U.S. PATENT DOCUMENTS

| 277,933 | A | | 5/1883 | Richmond |
|---|---|---|---|---|
| 973,343 | A | | 10/1910 | Corcoran |
| 2,596,941 | A | * | 5/1952 | Quintella ..................... 433/171 |
| 3,716,918 | A | | 2/1973 | Tole et al. |
| 3,987,546 | A | * | 10/1976 | Trampe ....................... 433/213 |
| 4,580,980 | A | | 4/1986 | Acquanetta |
| 4,657,509 | A | * | 4/1987 | Morris ......................... 433/37 |
| 4,764,115 | A | | 8/1988 | Willits et al. |
| 5,018,533 | A | | 5/1991 | Hawkins |
| 5,324,198 | A | * | 6/1994 | Hazen ......................... 433/171 |
| 5,951,291 | A | * | 9/1999 | Albert et al. ............... 433/215 |
| 6,079,981 | A | * | 6/2000 | Sekendur .................... 433/171 |
| 6,267,596 | B1 | * | 7/2001 | Kalfas ......................... 433/178 |
| 6,454,565 | B2 | * | 9/2002 | Phan et al. .................... 433/6 |
| 6,790,035 | B2 | | 9/2004 | Tricca et al. |
| 6,799,969 | B2 | | 10/2004 | Sun et al. |
| 6,896,516 | B2 | | 5/2005 | Lin et al. |
| 2003/0129565 | A1 | * | 7/2003 | Kaza ........................... 433/213 |

* cited by examiner

*Primary Examiner*—Cary E. O'Connor
(74) *Attorney, Agent, or Firm*—O'Melveny & Myers LLP (57) ABSTRACT

An appliance fabricated to improve the appearance of a patient's smile includes a plurality of simulated teeth. The interior surfaces of each of the teeth closely fits and conforms to the surface of a patient's real teeth while the outer surfaces of each of the simulated teeth has an ideal surface configuration. The dental appliance provides the patient with the appearance of a perfect set of teeth and an ideal smile without a need to alter the dental structure of the patient's teeth.

9 Claims, 8 Drawing Sheets

DENTAL APPLIANCE

RELATED APPLICATIONS

This application claims the benefit of U.S. Provisional Patent Application No. 60/665,343 filed Mar. 25, 2005, and U.S. Provisional Patent Application No. 60/666,203 filed Mar. 28, 2005.

FIELD OF THE INVENTION

The present invention relates generally to the field of dentistry and more particularly, to a dental appliance which can easily be applied to improve the smile of a patient.

BACKGROUND OF THE INVENTION

For years, dentistry has been evolving and has seen huge technological advances. Included among these advances are extreme makeovers with the use of bridgework or veneers as well as implants to replace the missing teeth. These reconstructions have a number of drawbacks:

Typical reconstruction procedures include a need to drill down healthy tooth structures. This is done to allow the seating of the artificial material either on or around the teeth. Some patients have a severe problem allowing a dentist to drill down natural tooth structure to accommodate something cosmetic. Healthy tooth structure is the most congenial and disease preventing material we can place near or over gingival gum tissue. Typical cosmetic reconstructions require removal of tooth structure to accommodate the reconstructive veneer. Typical veneers need anywhere from ½ to 1 mm in thickness of porcelain to be bonded onto the tooth.

Once a tooth, whether it be for a crown or an implant or even a veneer is subjected to reconstruction or a restorative procedure, the material or enamel that was taken away by a high powerful electric, air driven, hand piece can never grow back. This means that these dental fixtures or restorations must be redone over time.

The procedures used for cosmetic purposes must make room for the cosmetic materials. Therefore, there is a need for drilling of tooth structure and this tooth structure can never come back.

These prosthesis are placed on a fluid, oral cavity and conditions change over time. Over time, the gingival tissue changes and there is erosion of other teeth. As a result, there will be a need for changing these prosthetics over time. When teeth are drilled, there is only a matter of time or distance from the pulp cavity that would require the need for root canal treatment.

Initial placement of these cosmetic appliances will require extensive amount of time and effort to keep them clean and healthy. Whether it be veneers or bridgework, extra time at home is needed to take care of one's appliance.

If a patient is seeking to improve their smile, whether it be for an occasion or for a look they are trying to attain, unless that patient has perfect teeth and wants them whitened, the patient must go through an extensive makeover.

When someone desires a smile makeover, they are at the hands of the clinician. There is no trial run to see the esthetic result. A patient may want to have a say in the aesthetics, e.g., size, shape and contours, but once a conventional dental device is bonded, there is no going back.

OBJECTS AND SUMMARY OF THE INVENTION

It is an object of the present invention to provide an easily applied dental appliance which results in the patient having a beautiful smile.

Another object of the present invention is to provide a dental appliance which can be considered to be non-invasive.

Another object of the present invention is to provide a dental appliance which does not require removal of any portions of the patient's teeth.

Another object of the present invention which does not rely on bonding or cementing in order to be retentive in the patient's mouth.

Another object of the present invention is to provide a dental appliance which does not require any destruction or preparation of the tooth structure to facilitate a tight immovable fit.

Another object of the present invention is to provide a dental appliance which utilizes the surface configuration of the patient's natural dentition for retention.

Another object of the present invention is to provide a dental appliance which requires only two dental visits.

Another object of the present invention is to provide a dental appliance which allows an evaluation of a cosmetic treatment prior to an invasive procedure being performed on a patient's teeth.

Another object of the present invention is to provide a dental appliance which can be fabricated either from molar to molar incorporating up to fourteen teeth on each arch or for as few as eight teeth.

Another object of the present invention is to provide a dental appliance which will rest at the gingival margin or gum tissue thereby causing no periodontal disease.

Another object of the present invention is to provide a dental appliance which can be easily removed and reinstalled by the patient.

Another object of the present invention which can be used, in selected cases, to replace missing teeth.

Another object of the present invention is to provide a dental appliance which is both economical and cost effective.

Yet another object of the present invention is to provide a dental appliance which provides an effective smile makeover which is reversible and allows for future conventional dental procedures.

Other objects and advantages of the present invention will be made clear hereinafter.

In accordance with the invention, there is provided a dental appliance which includes a plurality of simulated teeth. The interior surfaces of each of the teeth closely fit and conform to the surface of a patient's real teeth while the outer surfaces of each of the simulated teeth present an ideal surface configuration. The dental appliance provides the patient with the appearance of a perfect set of teeth and an ideal smile without a need to alter the dental structure of the patient's teeth.

BRIEF DESCRIPTION OF THE DRAWINGS

Other important objects and advantages of the invention will be apparent from the following detailed description of the invention taken in connection with the accompanying drawings in which.

DETAILED DESCRIPTION OF THE INVENTION

Figure 1:
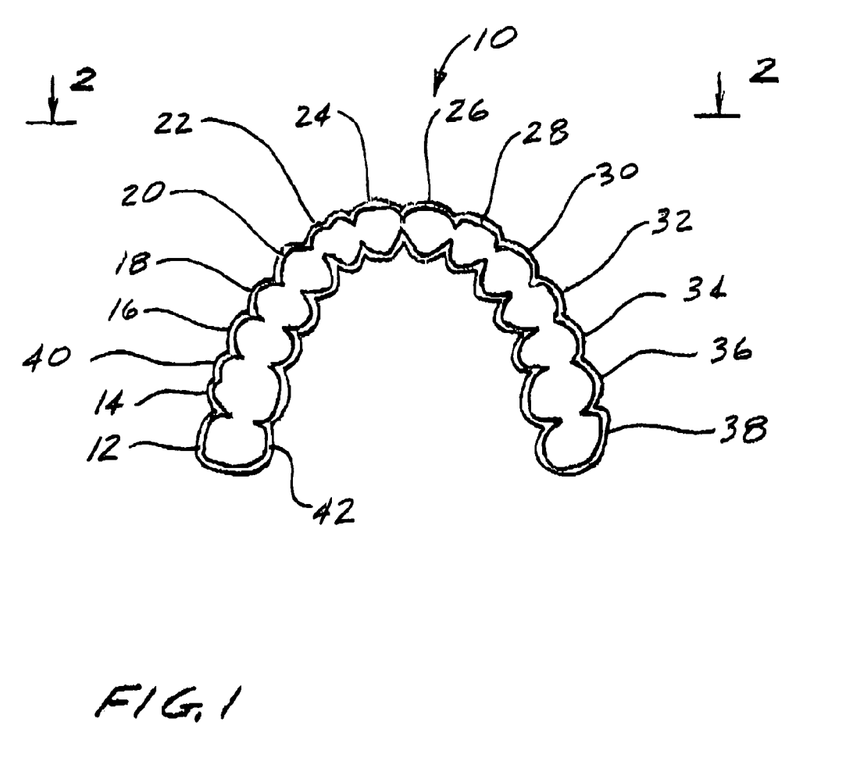
FIG. 1 is a top plan view of a dental device made according to the present invention.
Figure 2:
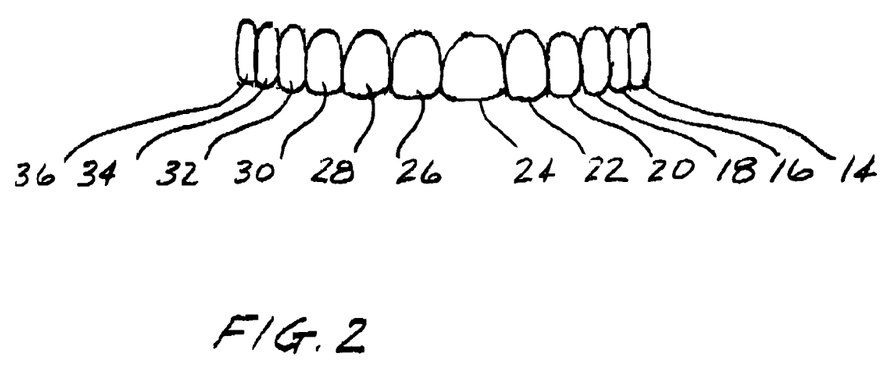
FIG. 2 is a front view of the dental device of FIG. 1 taken along the line 2-2 of FIG. 1.

With reference to the drawings, there is shown in FIG. 1 a dental appliance 10 made in accordance with the following invention.

The dental appliance 10 comprises a plurality of simulated teeth 12, 14, 16, 18, 20, 22, 24, 26, 28, 30, 32, 34, 36, 38 each of which is hollow. The interior surfaces of each of the teeth closely fits and conforms to the surface of a patient's real teeth while the outer surfaces 40 of each of the simulated teeth 12, 14, 16, 18, 20, 22, 24, 26, 28, 30, 32, 34, 36, 38 has an ideal surface configuration and conformance thereby providing the patient with the appearance of a perfect set of teeth and an ideal smile without a need to alter the dental structure of the patient's real teeth in any way. In the various Figs, the thickness of the walls 42 of the dental appliance has been exaggerated for purposes of clarity of illustration The detailed method of construction of the dental appliance including the securement and retention of the dental appliance to the patient's real teeth will be described presently.

Figure 3:
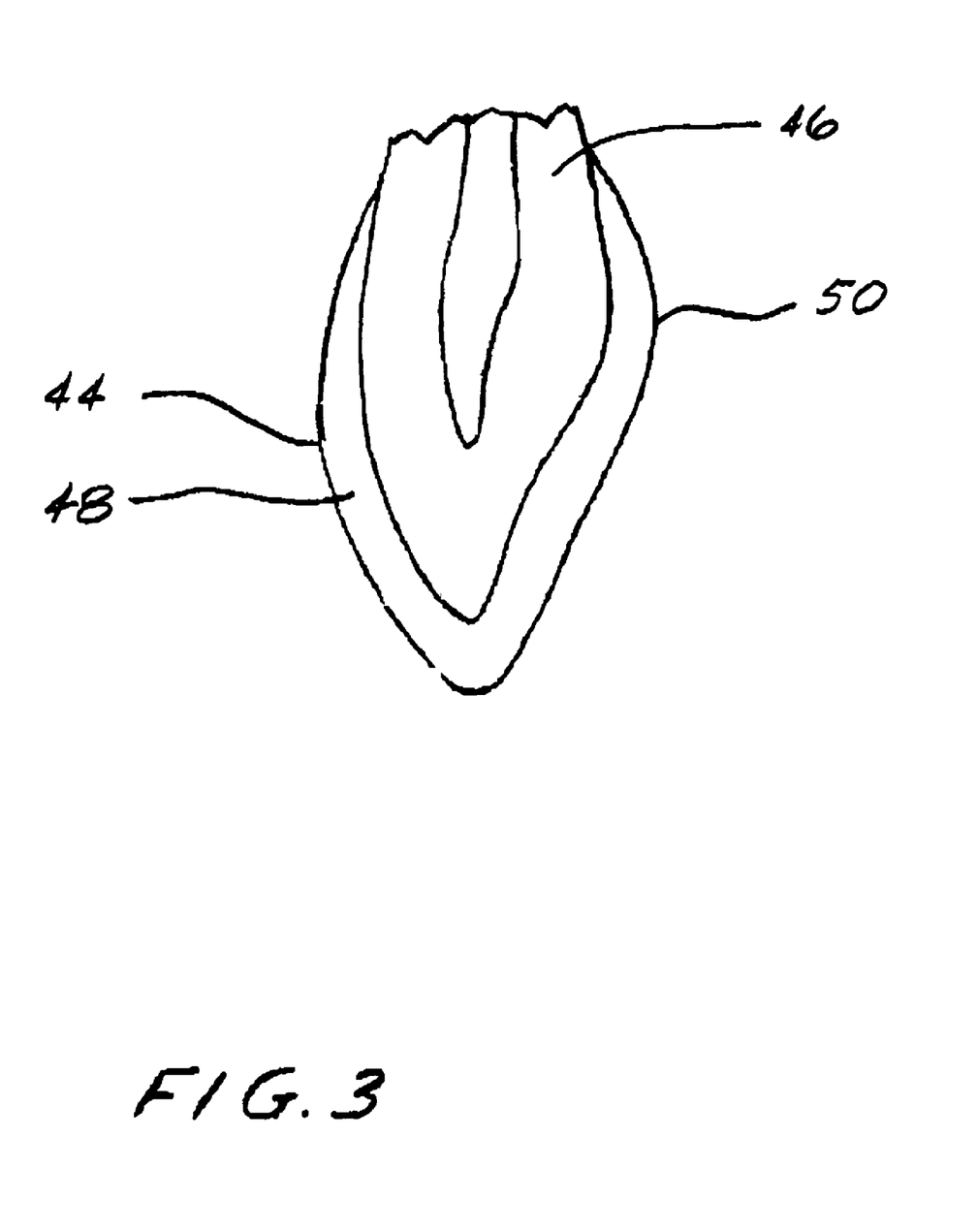
FIG. 3 is a cross-sectional view of a canine tooth showing the contour of the enamel.
Figure 4:
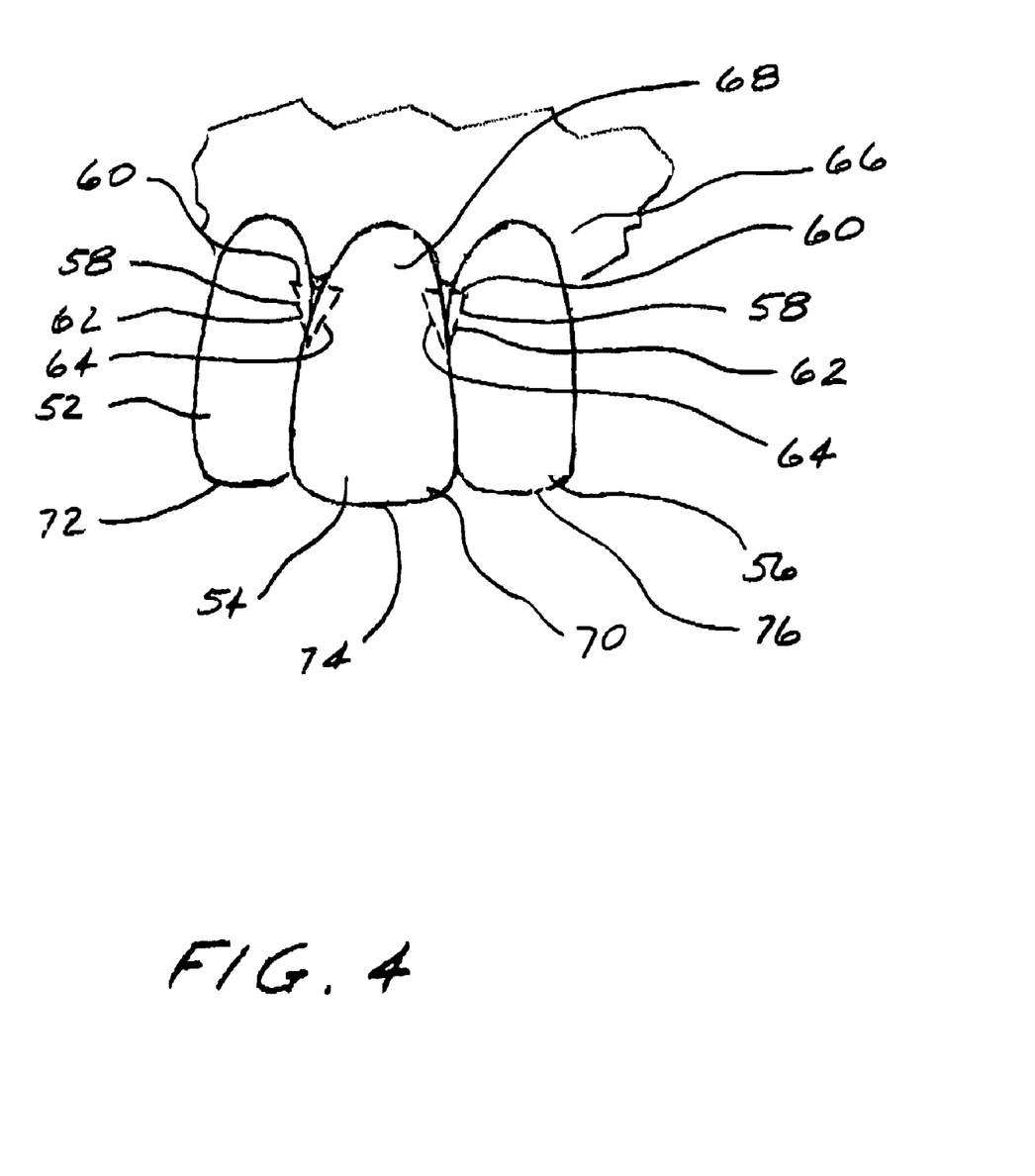
FIG. 4 is a fragmentary front view showing the retentive areas of a tooth.

Several key aspects of dental anatomy which relate to the retention of the dental appliance may be best understood with reference to FIG. 3.

As is best shown in FIG. 3, all teeth have what are called contours as well as interproximal areas. Each tooth in a patient's dentition has its own unique shape which lends itself to have a certain protrusion or a bulge at a certain location of the tooth. For example, if we look at the area designed by the reference numeral 44 on this particular tooth 44, which happens to be an upper canine or the eye tooth, we see what we call the height of contour of the tooth with the pronounced amount of enamel 48. This happens to be on the facial aspect of the tooth 44 or the cheek side.

The area designated by the reference numeral 50 indicates that there is a height of contour on the lingual or tongue side of the tooth as well. For retentive purposes, these contours are extremely important and will be explained in further detail.

Another aspect of the retentive properties resulting from the use of a patient's own detention is what in the dental profession is referred to as the interproximal or area in between the tooth themselves.

Figure 5:
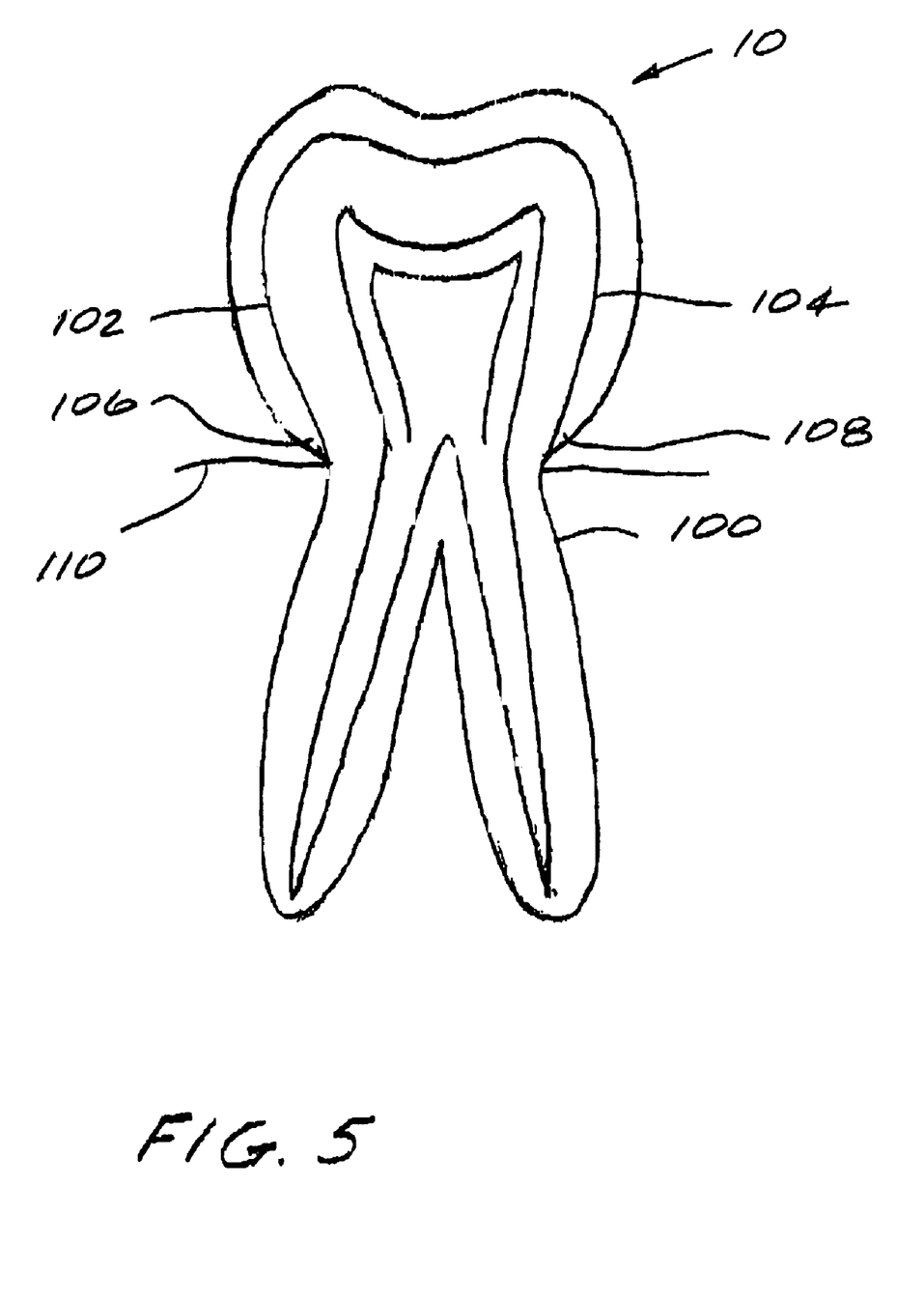
FIG. 5 is a cross-sectional view of a tooth showing retentive areas.

With reference to FIG. 5, which illustrates of some anterior teeth 52, 54, 56 of a typical dentition, we can have an understanding of the importance of the interproximal area 58. This area or zone is the triangle indicated by the broken lines 60, 62, 64 and is designated generally by the reference numeral 58 and is defined as the area between the teeth 52, 54 and 54, 56 which is created by the emergence profile of the teeth 52, 54, 56. This profile is established by anatomical formation of teeth 52, 54, 56 coming out of the gingival gum 66 and then flaring out to give a tooth its shape or body. As we can see, a tooth does not just form a box when it arises or erupts from the socket, rather it is thinner at the neck 68 of the tooth 54 and then fans or flares till it reaches its maximum height 70, resulting in a tooth that is wider at the top or what we refer to as an incisal or occlusal surface. The occlusal surfaces are generally designated by the reference numerals 72, 74, 76.

Figure 8:
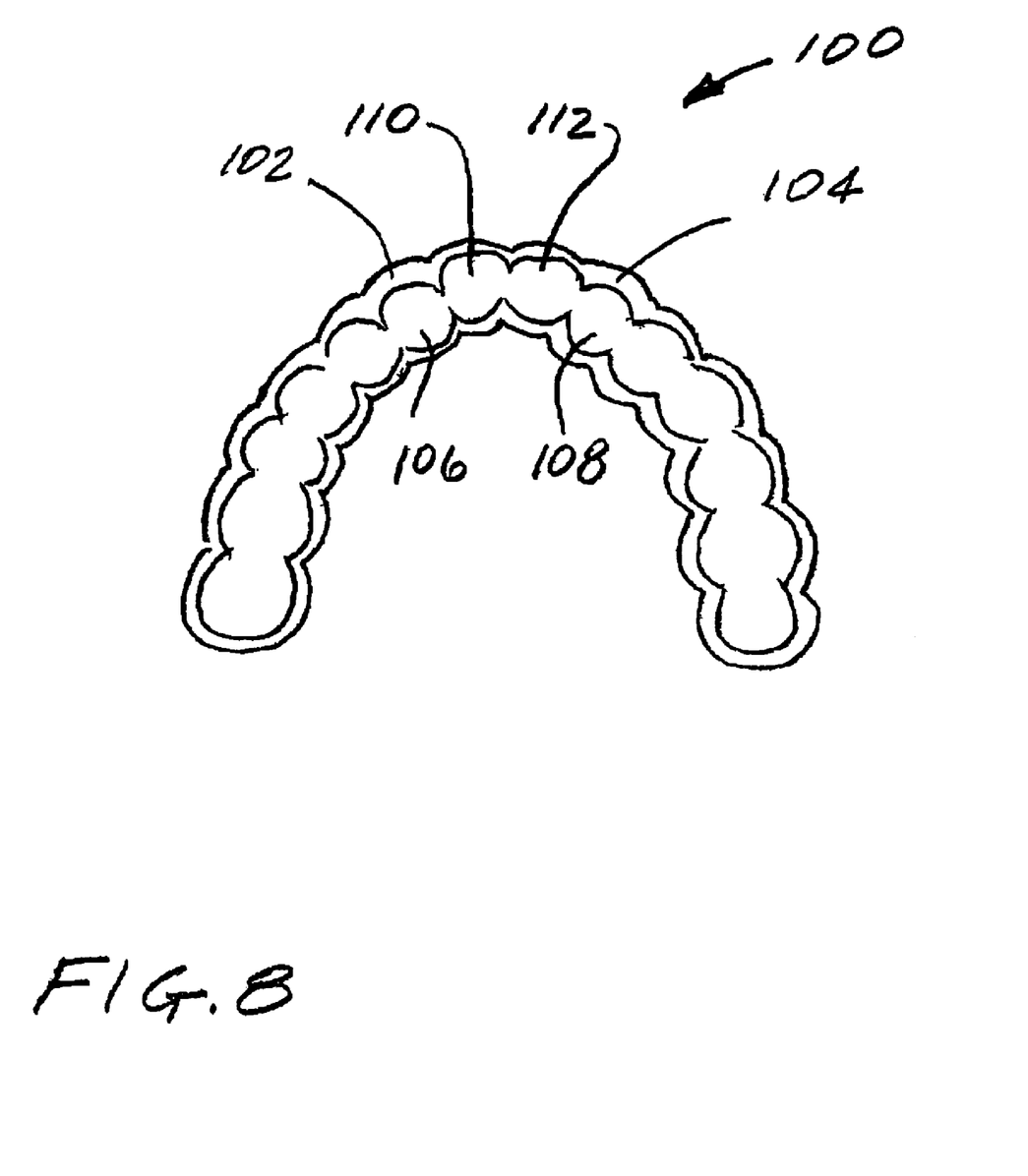
FIG. 8 is a top plan view similar to FIG. 1 showing a dental device which has been fabricated to compensate for lingual placement of incisors.

The thickness of the dental appliance 10 is decided by a number of factors. The thickness of some teeth is made thicker facially to have teeth in alignment from an aesthetic standpoint. A common example is when two lateral incisors are lingually placed and the patient has a desire to have his or her smile in complete conformity. As is shown in FIG. 8, the dentist will fabricate the dental appliance 102, 104 with the facial aspect of the two lateral incisors 106, 108 thicker than any other of the front teeth 110, 112.

Figure 6:
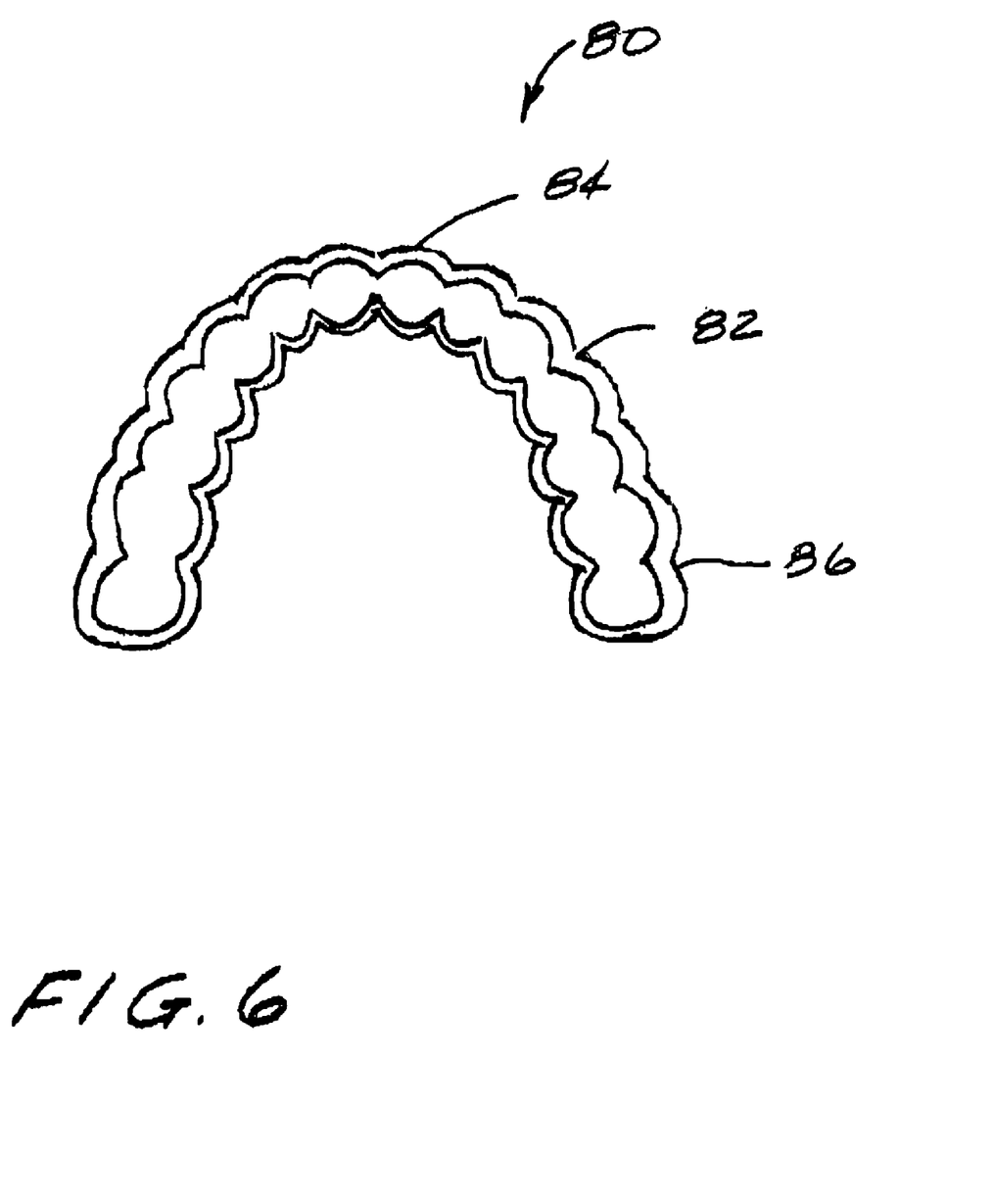
FIG. 6 is a top plan view similar to FIG. 1 showing a dental device which has been fabricated to provide the appearance of a wider smile.

Another example is termed "stepping out the smile." There is a very common situation when a tapered arch causes the patient to appear missing posterior teeth upon smiling. When the patient presents with this appearance, we attempt utilizing the dental appliance to bulk out the posterior aspect, to give the patient the appearance and the result of someone who has a more conformed aesthetically pleasing smile. The clinician and the dental technician would create a thicker facial aspect as the dental appliance 80 goes from anterior to posterior. This has been illustrated in FIG. 6 in which the thickness of the wall 82 has been progressively increased from anterior 84 to posterior 86.

Figure 7:
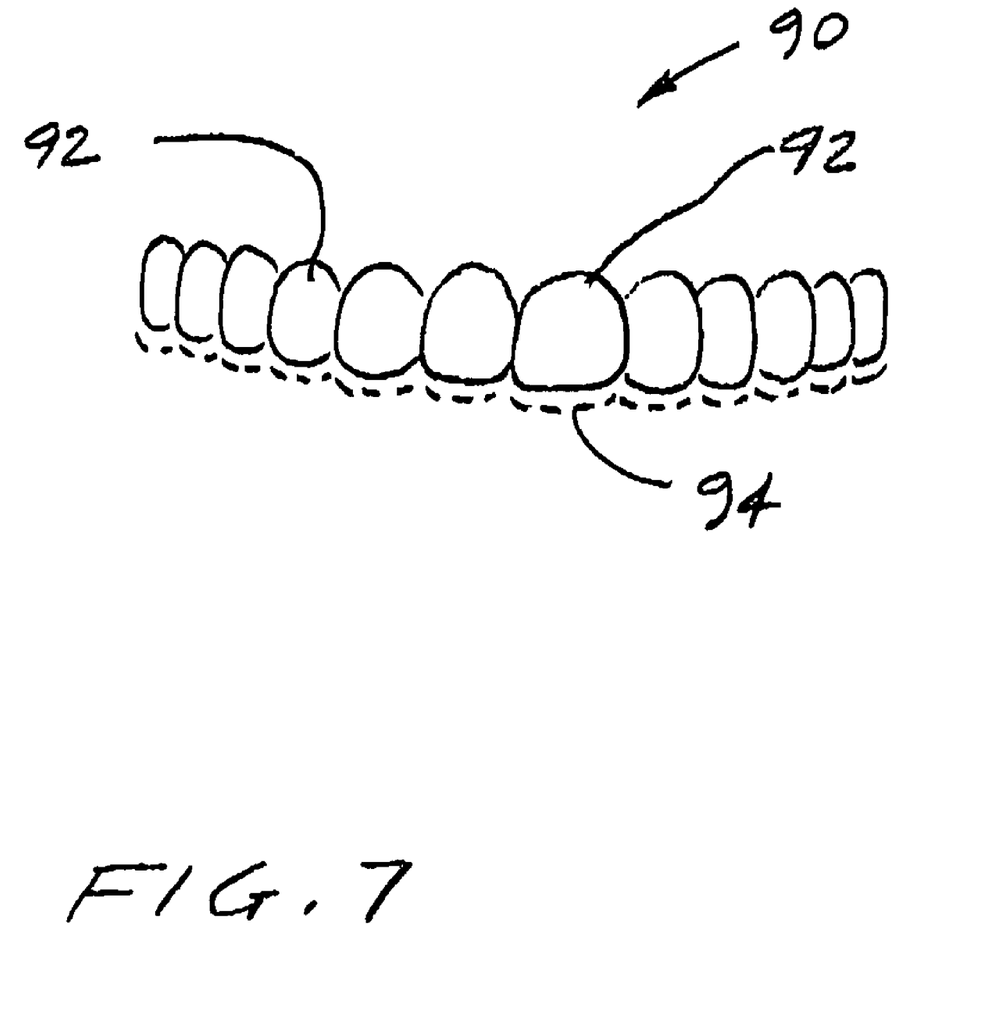
FIG. 7 is a front view similar to FIG. 2 showing the use of the dental appliance to increase the vertical dimensions of the teeth.

Another example relates to increasing the vertical dimension of the teeth. This is an extremely important application for the dental appliance 10. A common occurrence in dentistry is a result of severe grinding or bruxism. The only tissue or structure that creates facial weight is a person's teeth. Through the years, as a patient grinds or bruxes his or her teeth, teeth surface is lost and the teeth become shorter and so does a patient's vertical dimension or facial height. This can cause a tremendous stress on the tempro-mandibular joint. In the past, the common treatment was to use the crown and bridge modality and cap or crown the teeth to restore facial height. This treatment is done firstly through the use of acrylic temporaries and this necessitates the doctor to drill down the teeth to place these crowns even for the use of temporary crown. Through the years, many patients would be extremely apprehensive about committing to such a treatment without knowing the final vertical or facial height. With the dental appliance 90 according to the present invention, the dentist can use the appliance 90 to increase vertical dimension and achieve over the same time period that conventional crown and bridge dentistry takes to create a proper vertical dimension and facial height. This has been illustrated in FIG. 7. In FIG. 7, the increased vertical dimensions of the teeth, which are indicated typically by the numeral 92, has been indicated by the broken line 94.

The dental appliance 90 can gain more patient compliance and treatment plan acceptability as well as achieve the same result without committing the patient to irreversible crown and bridge therapy. Like any other method of treatment, careful record taking and treatment planning must be accomplished before dentist and patient choose the correct choice of treatment.

In cases of use of the dental appliance 90, the increase of vertical dimension, the clinician instructs the technician to increase thickness on the occlusal aspects and through proper bite records, the appliance can be made properly.

The dental appliance 10 is made of acetyl resin which is much more durable than acrylic, and which is what conventional crown and bridge temporaries are fabricated of In some types of cases, when it is a long term treatment, the dental appliance would offer the patient more aesthetics and comfort, as well as the knowledge that this treatment is totally reversible if so desired.

The dental appliance 10 has been tested on over 300 patients. The patients seem to accommodate the appliances added thickness quite well and this seems to be achieved via the design of the appliance. First, the dental appliance 10 can be made as thin as 0.4 mm in thickness so that the dental appliance, by itself, can create almost no interference with the occlusal aspect. Secondly, the design of the dental appliance is such that the liquid/aspect of the tooth of an upper arch has what we termed occlusal windows. These allow the supporting cusp to protrude out of these windows creating intercuspation of the two arches, so to allow the patient to fully close. The dental appliance 10 also enables patients to chew food and allows them to utilize the appliance for extended periods of time.

The dental appliance 10 allows the patients to wear the appliance without having the need to use any adhesive or cement or the preparation of a patient's existing teeth.

The points of retention of the dental appliance 10 are best shown in FIG. 5 in which a typical tooth 100 is shown. The dental appliance 10 is engaged onto the tooth and rides over the bulge 102 or height 104 of the contour of the tooth 100. The dental appliance 10 flaxes outwardly as this occurs and then settles right under this height of contour and returns to its original configuration thereby creating the retentive points 106, 108.

The retentive points 106, 108 are all supra gingivital and do not impinge into the gingival tissue 110.

The utilization of the height 102, 104 of the contour of the tooth 100 by the dental appliance 10 results in an extremely large amount of retention capability. This retention capability ensures that the dental appliance 10 will remain securely in place during all normal activities.

In a typical case where the dental appliance 10 covers twelve teeth, there are 24 areas or surface of retention.

As indicated previously, a preferred material for the dental appliance 10 has been found to be acetyl resin. Acetyl resin in crystallized form has a property which may be defined as "memory." This property allows the dental appliance to flex in order to ride over the contour of the tooth and then flex back to its original configuration after the dental appliance encounters the hard tooth structure. When it flexes back to encounter this hard structure, very strong retentive points are created, thus preventing the appliance from falling out or slipping even during mastication.

The outer surfaces of the dental appliance 10 are made as thick as the oral cavity will allow. For instance, the space between the outer surface of a tooth and the inner surface of the lip defines the space in which the dental appliance can reside. If the outer surface of the dental appliance is too thick, then the inner surface of the lip will be irritated. The outer surfaces of the dental appliance are polished to the highest possible degree in order to prevent irritation and to prevent accumulation of tartar. The thickness of the outer surface is also generally in line with the facial contours of the other teeth. For instance, if the dental appliance covers eight teeth, then the teeth on either side of the mid-line act as a guide for the thickness of the dental appliance.

In some cases, the dentist will fabricate the dental appliance 80 in a manner which will widen the smile by building out the buccal aspect (cheek side) of the dental appliance from anterior to posterior. An example of this type of case was shown in FIG. 6. These cases are accomplished when there is arch restriction of the teeth and there is sufficient space between the teeth and the cheeks.

The following steps are followed during the fabrication and installation of the dental appliance 10, 80, 90 according to the present invention.

Evaluating the patient's dentition and oral cavity, the focus is on the teeth and their strength. The most important contraindication to the application of the dental appliance is severe periodontal disease. Mild periodontal disease is not a problem as long as the teeth are not severely mobile.

Creating an accurate impression of the teeth using stock dental trays. The trays should not touch any of the tooth structure so that an accurate impression is formed of all of the tooth surfaces, including facial, buccal and lingual surfaces. Using a very accurate crown and bridge material preferably a polyether or a polyvinyl siloxane, an accurate impression is created of the entire arch for which the dental device is being fabricated.

Creating an impression of the counter arch. The material used for the counter arch impression may be standard alginate material.

Creating an accurate bite registration impression using reposil or other bite registration material.

Selecting the appropriate color and shade for the dental appliance in accordance with the desired visual impression to be created.

Using the various dental impression and bite registration impression, fabricating the dental appliance. The outer contours follow the general contours of the patient's dentition; however, the visible outer surfaces are fabricated to provide the desired visual effect by adjusting the thickness of the dental appliance as needed and adjusting the length and contour of each tooth to conform with an ideal standard as well as the aesthetics desired by the patient.

Installing the dental appliance by snapping the dental appliance over the patient's dentition into the aforesaid retentive areas.

Allowing the patient to sit with the dental appliance in place for several minutes in order to accommodate any slight settling, tongue adaptations and for any pressure areas to subside.

Checking the occlusion using disclosing paper.

Performing occlusion adjustments if needed.

Polishing any areas of the dental appliance which have been adjusted.

The foregoing specific embodiments of the present invention as set forth in the specification herein are for illustrative purposes only. Various deviations and modifications may be made within the spirit and scope of the invention without departing from the main theme thereof.

What is claimed is:

1. A dental appliance for improving appearance of a patient's teeth, comprising:
   a continuous wall that engages facial and lingual surfaces of the patient's teeth and provides a desired visual impression including a selected color and a selected contour, the wall comprising:
   an inner surface adapted to engage with the facial and lingual surfaces of the patient's teeth; and an outer surface comprising a tongue side arch and a visible cheek side arch, each of the arches extending from a first posterior location to an anterior portion and then to a second posterior location; and a plurality of retentive points for securing the dental appliance to the patient's teeth, the retentive points being supra gingivital;

wherein thickness of the wall between the inner and outer surfaces on the cheek side arch progressively increases toward the first and second posterior locations relative to the anterior location, thereby achieving the desired visual impression.

2. The dental appliance recited in claim 1, wherein the inner surface is further adapted to engage occlusal surfaces of the patient's teeth.

3. The dental appliance recited in claim 1, wherein a vertical aspect of the wall is configured to achieve the selected contour.

4. The dental appliance recited in claim 3, wherein the vertical aspect comprises an occlusal aspect.

5. The dental appliance recited in claim 1, wherein at least one of a facial aspect and a lingual aspect of the wall is configured to achieve the selected contour.

6. The dental appliance recited in claim 5, wherein the facial aspect is thicker than the lingual aspect.

7. The dental appliance recited in claim 1, wherein the wall is configured to build out a buccal aspect of the dental appliance from the anterior location to one of the first and second posterior locations.

8. The dental appliance recited in claim 1, wherein the desired visual impression comprises a selected shade.

9. The dental appliance recited in claim 1, wherein the dental appliance is made of acetyl resin.

* * * * *